United States Patent [19]

Janssen et al.

[11] 3,946,059

[45] Mar. 23, 1976

[54] METHOD OF PREPARING ALKYLALKOXYSILANES CONTAINING POLYSULFIDE BRIDGES

[75] Inventors: Paul Janssen, Bensberg-Refrath; Klaus-Dieter Steffen, Troisdorf-Oberlar, both of Germany

[73] Assignee: Dynamit Nobel Aktiengesellschaft, Troisdorf, Germany

[22] Filed: Dec. 3, 1974

[21] Appl. No.: 529,202

[30] Foreign Application Priority Data

Dec. 5, 1973  Germany............................ 2360471

[52] U.S. Cl. 260/448.2 E; 260/448.2 N; 260/448.8 R
[51] Int. Cl.² ..... C07F 7/04; C07F 7/08; C07F 7/18
[58] Field of Search ............... 260/448.2 E, 448.8 R

[56] References Cited
UNITED STATES PATENTS

| | | |
|---|---|---|
| 3,284,466 | 11/1966 | Rosenthal................ 260/448.2 E X |
| 3,317,461 | 5/1967 | Plueddemann........... 260/448.2 E X |
| 3,530,160 | 9/1970 | Gardner et al........... 260/448.2 E X |
| 3,768,537 | 10/1973 | Hess et al................ 260/448.8 R X |
| 3,842,111 | 10/1974 | Meyer-Simon et al....... 260/448.2 E |
| 3,873,489 | 3/1975 | Thurn et al.............. 260/448.8 R X |

*Primary Examiner*—Paul F. Shaver
*Attorney, Agent, or Firm*—Burgess, Dinklage & Sprung

[57] ABSTRACT

A process for preparing an alkylalkoxysilane containing polysulfide bridges which silane has the formula:

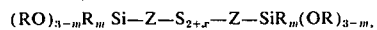

wherein R represents identical or different linear or branched alkyl radicals having 1 to 6 carbon atoms or phenyl, Z represents linear or branched alkylene radicals having 1 to 8 carbon atoms, $m$ is 0 to 3 and $x$ is 1 to 4, which comprises contacting a bis-alkyl-alkoxysilyldisulfide of the formula:

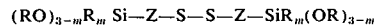

wherein R, Z and $m$ have the previously assigned significance, with sulfur at a temperature between 100° and 200°C.

10 Claims, No Drawings

METHOD OF PREPARING ALKYLALKOXYSILANES CONTAINING POLYSULFIDE BRIDGES

BACKGROUND OF THE INVENTION

1. Field of the Invention

This invention relates to the preparation of alkylalkoxysilanes having polysulfide bridges wherein there are more than 2 sulfur atoms in the molecule. This invention is particularly directed to the preparation of bis-(alkoxylalkylsilyl)-polysulfides particularly bis-[γ-(trialkoxysilyl)-alkyl] polysulfides of at least 3 sulfur atoms in the compound.

2. Discussion of the Prior Art

The preparation of sulfurous silanes of the type named is already known. These compounds are useful as adhesivizers in sulfur-vulcanizable-rubber mixtures reinforced with organic materials such as glass, silicon dioxide and the like.

Methods for the preparation of these compounds are also known. One such method involves reacting a mercaptosilane with a sulfur chloride or with the oxidants bromine, iodine, thionyl chloride or dialkyl sulfoxides which are known agents for the dehydrogenation of mercaptans to disulfides. Such a process is described in Houben-weyl, Houben-Weyl, Methoden der organischen Chemie", 4th Ed., 1959, vol. 9, pages 59–65. However, such a process for the preparation of sulfurous silanes suffers from the disadvantage that the sulfur chlorides employed are sensitive to moisture, decompose readily and especially in the case of $S_2Cl_2$, have an unpleasant lachrymatory odor. When dialkyl sulfoxides are used it is also disadvantageous in that water is formed during the reaction. This so formed water reacts with the alkoxy group of the silane resulting in hydrolysis thereof and simultaneous formation of siloxanes of higher molecular weight.

Another method for the preparation of these compounds utilizes chloralkylsilanes which are reacted with alkali sulfides or polysulfides. Such a process is described in German Offenlegungsschrift No. 2,141,159. The disadvantage of this method lies in the fact that it is necessary to separate the alkali chloride that forms and consequently an additional step is involved in the process with its corresponding investment in time and apparatus.

All known methods are, furthermore, encumbered by the disadvantage that they are best performed in a solvent, preferably at elevated temperature. Consequently for the isolation of the product, the solvent must be removed by an additional separation procedure.

It has, therefore, become desirable to provide a process for the preparation of alkylalkoxysilanes having polysulfide bridges which process can advantageously be carried out in the absence of a solvent, does not yield water which will interfere with the alkoxy group on the silane, does not utilize a reactant which can easily decompose and does not involve the creation of unpleasant, noxious or lachrymatory odors.

SUMMARY OF THE INVENTION

Broadly, this invention contemplates a process for the preparation of an alkylalkoxysilane containing a polysulfide bridge having the formula:

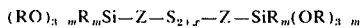

wherein each R represents an identical or different linear or branched alkyl radical having 1 to 6 carbon atoms or phenyl, Z represents a linear or branched alkylene radical having 1 to 8 carbon atoms, m is 0 to 3 and x is 1 to 4, which comprises contacting a bis-alkyl-alkoxysilyldisulfide of the formula:

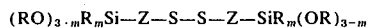

wherein R, Z and m have the previously assigned significance, with sulfur and a temperature between 100° and 200°C.

It has been advantageously discovered that by reacting a bis-alkyldisulfide with sulfur at the indicated temperatures that the reaction can be advantageously carried out in the absence of a solvent. Moreover, it has been discovered that the process proceeds advantageously in the absence of a solvent, in contrast to the prior art procedures. The polysulfides thus obtained are viscous liquids of a dark red color. They possess high purity and can be used immediately without purification.

Although not wishing to be bound by theory, it is believed that during the process a structural arrangement or rearrangement of the sulfur atoms between the two silyl radicals may occur. It may be in the form of an S—S—S—S chain or it may be in the nature of a keto group having the formula

The amount of sulfur to be added depends on the number of sulfur atoms desired in the bridge. The corresponding stoichiometric amount is always used, and the polysulfide with the desired number of sulfur bridges forms predominantly as the end product. The reaction product, however, always still contains the next higher and lower sulfur homologs, as it has been found by mass spectrometry studies.

The reaction time depends on the temperature level selected. It is preferable to operate at temperatures between 120° and 160°C. The end of the reaction is indicated by the fact that no more sulfur crystallizes out as the reaction mixture cools. This is the case after 10 to 60 hours, depending on the reaction temperature. Any free sulfur that is still present can easily be detected by thin layer chromatography.

The bis-silyl disulfides to be used as starting products for the present process are also liquids which are prepared in a simple manner by reacting the appropriate silyl mercaptans with sulfuryl chloride in accordance with the reaction equation:

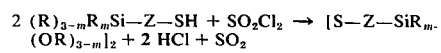

These compounds, contrary to the statements made in German Offenlegungsschriften Nos. 2,141,159 and 2,141,160, are distillable, colorless liquids. Accordingly, they can be used as pure compounds, so that the purity of the polysulfides obtained in accordance with the invention is greater than that of the silyl polysulfides prepared by the methods known hitherto.

A suitable method for the preparation of bis-[γ-(trialkoxysilyl)-propyl]-disulfides is disclosed in copending application Ser. No. 529,203 filed Dec. 3, 1974 entitled "Bis-[γ-(Trialkoxysilyl)-Propyl]-Disulfides of High Purity", the disclosure of which is hereby incorporated specifically herein by reference. According to the process therein disclosed such a disulfide can be prepared by reacting a γ-chloropropyl-triethoxy silane with thiourea and sodium iodide in alcohol for 24 hours at ebullition. After the reaction mixture is cooled to room temperature and over a period of 4 hours a strong current of ammonia is passed through the solution. This causes ammonium chloride to precipitate. The filtrate and precipitate are separated and the filtrate can be concentrated whereby to obtain γ-mercaptopropyl-triethoxy silane. This latter material can be reacted with sulfuryl chloride in a solvent such as anhydrous benzene at a temperature of +8 − + 12°C. The $SO_2Cl_2$ is added to the γ-mercapto-propyl-triethoxy silane dropwise over a period of about 55 minutes. Sulfur dioxide and hydrogen chloride gas which are formed are removed by a nitrogen gas purge. After a period of about 6 hours at room temperature with stirring triethylamine can be added whereby to precipitate the amine hydrochloride. The filtrate is then fractionally distilled whereby there is recovered a bis-[γ-(triethoxysilyl)-propyl]-disulfide.

In conducting the reaction of the present process the alkoxy radical in the bis-silyl-disulfide is preferably methyl, ethyl, butyl, methoxyethyl or ethoxyethyl. The preferred alkylene radical is the propylene group.

If the purity of the silyl polysulfides to be prepared in accordance with the invention is of lesser importance, one can combine the above-mentioned method of preparing the bis-silyl disulfides with the method of the invention. It is then preferable to proceed by bringing the silyl mercaptans to reaction with the sulfuryl chloride in a solvent in which sulfur is also soluble. The reaction is begun with the preparation of the disulfide, i.e., by combining the appropriate mercaptoalkyl silane with sulfuryl chloride in the presence of a solvent, and then, towards the end of the formation of hydrogen chloride and sulfur dioxide gas, adding the stoichiometrically necessary amount of sulfur at a slightly elevated temperature (up to about 60°). Preferred solvents are aromatic solvents such as benzene, toluene or xylenes. The temperature of the reaction mixture is then elevated to above 100°C, preferably to temperatures between 100° and 160°C, distilling the solvent away, until all of the sulfur has dissolved in the liquid and does not crystallize out again upon cooling. The product obtained is then directly usable.

In order to more fully illustrate the nature of the invention and the manner of practicing the same the following examples are presented.

EXAMPLES

Example 1

Bis-[γ-(triethoxysilyl)-propyl]-trisulfide 47.5 g of bis-[γ-(triethoxysilyl)-propyl]-disulfide (0.1 mole) was heated together with 3.2 g of sulfur (0.1 mole) under a nitrogen gas atmosphere for about 15 hours at about 150°C, until all of the sulfur had dissolved and did not crystallize out again upon cooling. A dark red liquid was formed, which a thin-layer chromatogram showed to contain no free sulfur, and in which disulfides and tetrasulfides are dissolved as shown by mass spectrographic analysis.

Sum formula: $C_{18}H_{42}O_6S_3Si_2$, molecular weight: 506.89.

Elemental analysis: Calculated: C, 42.68; H, 8.35; S, 18.98; Si, 11.08. Found: C, 41.92; H, 8.63; S, 18.70; Si, 11.47.

Example 2

Bis-[γ-(triethoxysilyl)-propyl]-tetrasulfide 47.5 g of bis-[γ-(triethoxysilyl)-propyl]-disulfide (0.1 mole) was heated together with 6.2 g of sulfur (0.2 mole) in a nitrogen gas atmosphere for about 50 hours at 160°C, until all of the sulfur had gone into solution and did not crystallize out again when the solution was cooled. A dark red, viscous solution was formed, which a thin-layer chromatograph shows to contain no more free sulfur, and which, according to mass spectrometric analysis, contains a small amount of pentasulfide in addition to disulfides and trisulfides.

Sum formula: $C_{18}H_{42}O_6S_4Si_2$, molecular weight: 538.96.

Elemental analysis: Calculated: C, 40.11; H, 7.85; S, 23.80; Si, 10.42. Found: C, 40.59; H, 7.81; S, 21.50; Si, 10.91.

Example 3

Bis-[γ-(trimethoxysilyl)-propyl]-trisulfide and
Bis-[γ-(trimethoxysilyl)-propyl]-tetrasulfide In a 500 ml. four-necked flask provided with stirrer, reflux condenser, dropping funnel and thermometer, 39.268 g of γ-mercaptopropyltrimethoxysilane (0.2 mole) was dissolved in 130 ml. of absolute benzene. 13.6 g of $So_2Cl_2$ (0.1 mole), dissolved in 20 ml. of benzene, was added drop by drop over a period of 30 minutes at 10°C, under a current of nitrogen gas. After this mixture had been stirred at room temperature for about 4 hours, 6.41 g of flowers of sulfur was added and the temperature was gradually raised by means of an oil bath to 150°C while the benzene was distilled out. The reddish brown liquid was kept at 150°C for about 24 hours and decanted to remove a few small crystals (melting point above 350°C). Yield: 45.5 grams (100% of the theory).

Thin layer chromatographic analysis showed the compound to contain no more free sulfur; mass spectroscopy shows it to consist of a mixture of di-, tri-, tetra- and penta-sulfides, most of them being tri- and tetrasulfides. Analytically, 24.1% sulfur is found; for a 1:1 mixture of tri- and tetrasulfide, 25.5% sulfur was calculated.

Example 4

Bis-[γ-(trimethoxyslyl)-propyl]-trisulfide 39.07 g of bis-[γ-(trimethoxysilyl)-propyl]-disulfide (0.1 mole) was heated under a nitrogen gas atmosphere together with 3.20 g of flowers of sulfur (0.1 mole) for about 24 hours at 150°C. A dark red liquid formed, which according to the mass spectrum contains di- and tetrasulfides, but no more free sulfur.

Sum formula: $C_{12}H_{30}S_3Si_2$, molecular weight 422.73. Calculated: C, 34.10; H, 7.15; S, 22.75; Si, 13.29. Found: C, 33.88; H, 6.74; S, 22.66; Si, 13.67.

What is claimed is:

1. A process for preparing an alkylalkoxysilane containing a polysulfide bridge having the formula:

wherein each R represents an identical or different linear or branched alkyl radical having 1 to 6 carbon atoms or phenyl, Z represents a linear or branched alkylene radical having 1 to 8 carbon atoms, $m$ is 0 to 3, $x$ is 1 to 4, which comprises contacting a bis-alkyl-alkoxysilyl-disulfide of the formula:

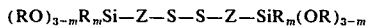

wherein R, Z and $m$ have the previously assigned significance, with the sulfur at a temperature between 100° and 200°C.

2. A process according to claim 1 wherein the disulfide and sulfur are maintained in contact with one another at a temperature between 120° and 160°C.

3. A process according to claim 1 wherein R is ethyl.

4. A process according to claim 1 wherein Z is propylene.

5. A process according to claim 1 wherein $m$ is 0.

6. A process according to claim 1 wherein the sulfur is present in at least a stoichiometric amount and $x$ is 1.

7. A process according to claim 1 wherein $x$ is 2 and sulfur is present in a stoichiometric amount. sulfuryl formula 8. A process according to claim 1 wherein $x$ is 3 and the sulfur is present in a stoichiometric amount.

9. A process according to claim 1 wherein the process is carried out in the absence of a solvent.

10. A process according to claim 1 wherein the disulfide is formed by contacting a silylmercaptan with a sulfuryl chloride in a solvent in which sulfur is also soluble and at the termination of the reaction between the silylmercaptan and the sulfur chloride sulfur is added to the reaction mixture containing, as the result thereof, a disulfide of the formula:

wherein R, Z and $m$ have the previously assigned significance and the reaction mixture is maintained at a temperature between 100° and 160°C.

* * * * *

UNITED STATES PATENT AND TRADEMARK OFFICE
CERTIFICATE OF CORRECTION

PATENT NO. : 3,946,059
DATED : March 23, 1976
INVENTOR(S) : Paul Janssen and Klaus-Dieter Steffen It is certified that error appears in the above-identified patent and that said Letters Patent are hereby corrected as shown below:

Column 1, line 27

"Houben-Weyl", first occurrence, should be deleted

Column 6, lines 2-3

"sulfuryl formula" should be omitted.

Signed and Sealed this twenty-ninth Day of June 1976

[SEAL]

Attest:

RUTH C. MASON
*Attesting Officer*

C. MARSHALL DANN
*Commissioner of Patents and Trademarks*